US008448928B2

(12) United States Patent
Weber

(10) Patent No.: US 8,448,928 B2
(45) Date of Patent: May 28, 2013

(54) DEVICE FOR HOLDING A MODEL SUPPORT OF AN ABUTMENT MODEL

(75) Inventor: Gerhard Weber, Pürgen (DE)

(73) Assignee: Straumann Holding AG, Basel (CH)

( * ) Notice: Subject to any disclaimer, the term of this patent is extended or adjusted under 35 U.S.C. 154(b) by 182 days.

(21) Appl. No.: 12/682,085

(22) PCT Filed: Oct. 2, 2008

(86) PCT No.: PCT/EP2008/008392
§ 371 (c)(1),
(2), (4) Date: Sep. 29, 2010

(87) PCT Pub. No.: WO2009/049778
PCT Pub. Date: Apr. 23, 2009

(65) Prior Publication Data
US 2011/0020764 A1 Jan. 27, 2011

(30) Foreign Application Priority Data
Oct. 9, 2007 (DE) .......................... 10 2007 048 356

(51) Int. Cl.
*A61C 13/12* (2006.01)
(52) U.S. Cl.
USPC ...................................... 269/8; 29/559; 269/6
(58) Field of Classification Search
USPC ................................................ 269/8, 6, 3, 95
See application file for complete search history.

(56) References Cited

U.S. PATENT DOCUMENTS

| 2005/0060868 A1* | 3/2005 | McMurtry ...................... 29/559 |
| 2006/0093204 A1 | 5/2006 | Holzner et al. |
| 2006/0115784 A1 | 6/2006 | McMurtry et al. |
| 2008/0108014 A1 | 5/2008 | Holzner et al. |

FOREIGN PATENT DOCUMENTS
DE 3117506 A1 11/1982
(Continued)

OTHER PUBLICATIONS

Office Action in related German Patent Application 10 2007 048 356.4-43 dated Apr. 21, 2008 from the German Patent Office.
International Search Report in corresponding PCT/EP2008/008392 filed Oct. 2, 2008.

(Continued)

*Primary Examiner* — Lee D Wilson
*Assistant Examiner* — Melanie Alexander
(74) *Attorney, Agent, or Firm* — Novak Druce Connolly Bove & Quigg LLP

(57) ABSTRACT

The invention relates to a device for holding a model support of an abutment model and also to an insert (1) for holding such a model support, with a first area and a second area, wherein the first area comprises a flat surface (6) with a step (4) at the center of which there is an area which has an attachment geometry of an implant and onto which the model support of the abutment model can be mounted, wherein the second area comprises means that permit positioning of the insert, and wherein the insert comprises an optically detectable marking (5). The invention additionally relates to a pot (13) for receiving an insert according to the invention, wherein the pot comprises at least one magnet (18) and at least one recess and/or elevation on the bottom surface. The invention also relates to a scanning device, a scanning method, a method for producing an abutment, a method for producing a tooth replacement part, and a computer-readable medium.

11 Claims, 4 Drawing Sheets

FOREIGN PATENT DOCUMENTS

| | | |
|---|---|---|
| DE | 202005003439 U1 | 7/2005 |
| DE | 196 24 963 A1 | 1/2008 |
| EP | 1719473 A2 | 11/2006 |
| EP | 1820469 A1 | 8/2007 |
| EP | 1920731 A | 5/2008 |

OTHER PUBLICATIONS

English Translation of the International Preliminary Report on Patentability mailed May 11, 2010 in corresponding PCT/EP2008/008392.

* cited by examiner

DEVICE FOR HOLDING A MODEL SUPPORT OF AN ABUTMENT MODEL

FIELD OF THE INVENTION

The invention relates to a device for holding a model support of an abutment model, an insert for holding a model support of an abutment model, a pot for receiving an insert for holding a model support of an abutment model, a scanning device, a scanning method, a method for producing an abutment, a method for producing a tooth replacement part comprising an abutment as well as a computer-readable medium.

BACKGROUND

Devices for scanning tooth models for obtaining a data record which represents the tooth model are well-known. These data records can be used for the automated production of tooth replacement parts.

SUMMARY OF THE INVENTION

Moreover, the modeling of tooth replacement parts, such as an abutment, is well-known. An abutment is a part of a dental provision which is applied onto an implant. For example, a crown or a bridge can be mounted onto the abutment.

It is the object of the present invention to provide apparatus and methods that permit an automated production of individual abutments or other tooth replacement parts.

A device for holding a model support of an abutment model can comprise a holder and receiving means, wherein the holder can comprise at least one magnet and/or a magnetic material, and wherein the holder can be mountable onto the receiving means, and wherein the holder can be variably positioned with respect to the receiving means. As no exact positioning of the holder with respect to the receiving means is required, positioning can be accomplished very easily, for example even without any tool.

This is advantageous, for example, in non-rotatory scanning methods, in particular in at least partially translatory scanning methods, for example with a Cartesian coordinate system, wherein thus for example no exact centering relative to an axis of revolution is necessary.

The holder can comprise at least one magnet, and the receiving means can comprise at least one magnet and/or a material which is attracted by the at least one magnet of the holder, or the holder can alternatively comprise at least one magnetic material and the receiving means can comprise a magnet. The magnetic interaction between the holder and the receiving means can permit a restricted prepositioning effect which permits, for example, positioning without tools. In the device according to the invention, the holder and the receiving means can be formed each such that variable positioning is only possible within a restricted area. This serves, for example, to give software that must process obtained scanning data an indication stating within which area of the scanning data one has to look for certain features. The area can be, for example, more than 1, 2 or 3 mm and/or less than 7, 6, 5, 4 or 3 mm in one direction in space and/or in two and/or in three directions in space perpendicular with respect to each other.

A restricted prepositioning effect can also result, for example, from at least two pairs of complementary oriented magnetic poles. The pairs of magnetic poles can be arranged such that they repel each other in one pair combination and attract each other in another pair combination. In a preferred embodiment, at least two different magnetic poles can be provided at the holder and at least two different magnetic poles can be provided at the receiving means for this.

Here, the area to which variable positioning is restricted can have different dimensions in different directions in space. For example, the receiving means can be located in the x-y plane and comprise, for example, a groove or a recess and/or elevation of any other shape oriented in the x direction. The holder to be mounted can comprise a groove, recess and/or elevation with a correspondingly reversed shape. If the holder is then mounted onto the receiving means, the positioning of the holder can be restricted in the y direction, but still remain variable in the x direction (within certain limits). This, too, assists the software in recognizing certain features, while handling remains easy.

For example, the distance between the holder and the receiving means can be predetermined by the shape of the holder and the receiving means. If the device of holder and receiving means is, for example, scanned, no distance regulation of the scanning device is necessary, thereby facilitating the scanning process.

The holder and/or the receiving means can comprise each at least one groove, one flute, one hole, one pin, one peg, one recess and/or one elevation. Thereby, a relative position of the holder and the receiving means can be determined. Moreover, the variable positioning of the holder with respect to the receiving means can be restricted thereby.

In this case, the at least one groove, the at least one flute, the at least one hole, the at least one pin, the at least one peg, the at least one recess and/or the at least one elevation of the holder can be shaped to be reversed with respect to those of the receiving means.

The holder can comprise a first and a second area, wherein the first area comprises a flat surface, wherein a step is located on or in the flat surface in the center of which there is an area that comprises an attachment geometry of an implant and onto which the model support of the abutment model can be mounted, and wherein the second area comprises means that permit the positioning of the holder. By means of the step, for example the height of the abutment model relative to the attachment geometry can be determined.

Moreover, the holder can comprise an optically detectable marking. By such a marking, the position of the model support of the abutment model relative to the marking and/or to the attachment geometry of the implant can be, for example, very precisely identified.

Furthermore, the holder can comprise at least one gripping device in the first area which preferably starts from the flat surface. By means of this gripping device, the holder can be gripped, for example, to be mounted onto the receiving means, however, the gripping device can also be used to move the holder.

An insert for holding a model support of an abutment model can comprise a first and a second area. The first area can comprise a flat surface, wherein a step can be located on or in the flat surface in the center of which an area can be located which can comprise the attachment geometry of an implant and onto which the model support of the abutment model can be mounted. The second area can comprise means which can permit to position the insert. Moreover, the insert can comprise an optically detectable marking.

The insert can comprise at least one magnet in the second area. The magnet of the insert can be used to pull the insert into another component or towards another component which also comprises a magnet, wherein the other component can, for example, receive the insert.

The insert described above can be in particular provided as a holder as it is used in the above-described device for holding a model support of an abutment model.

The at least one magnet in the second area of the insert can be located below the area which comprises an attachment geometry of the implant and onto which the model support of the abutment model can be mounted if the flat surface of the insert lies horizontally and faces upwards. The insert can also comprise, for example, two, three, four or more magnets in the second area. The magnet or magnets in the described embodiments permit a flexible and easy-to-handle mounting of the insert. In this connection, reference is made to the pairs of magnetic poles oriented in opposite directions as described above.

The optically detectable marking can be located on the flat surface. This can prevent the marking from being covered, for example by the model support of the abutment model.

The cross-section of the insert can be circular. The cross-section of the insert, however, can also be square, rectangular, triangular, hexagonal, polygonal or elliptic or have any other shape.

In the second area, the insert can comprise at least one groove, one flute, one hole, one pin, one peg, one recess and/or one elevation. Thereby, a relative position of the insert can be determined. If there are grooves, flutes, holes, pins, pegs, recesses and/or elevations with a correspondingly reversed shape in another component into which the insert can be inserted, for example, the relative position of the insert with respect to the other component can be determined.

Preferably, the insert can comprise, for example, two grooves, flutes, holes, pins, pegs, recesses and/or elevations in the second area, which can preferably have different dimensions.

The insert can comprise at least one gripping device in the first area which can preferably start from the flat surface. The gripping device can be used to grip and/or move the insert. Moreover, the gripping device can be embodied such that the position for example of the step and/or the optically detectable marking relative to the gripping device is clearly determined.

The at least one gripping device can project obliquely, starting from the flat surface. By the oblique course of the gripping device, the area with the mounted model support of the abutment model can be prevented, for example, from being covered.

The at least one gripping device can project beyond a limit of the flat surface. This can prevent, for example, the optically detectable marking from being covered.

The optically detectable marking of the insert can be located at equal distances between an edge of the step and an edge of the flat surface. By the determination of the relative position of the optically detectable marking, for example a scanning operation for detecting the marking can be restricted to a certain area of the flat surface and thereby facilitated.

The optically detectable marking can comprise a pin, a peg, a hologram, a bar code, a pattern code, a groove, a flute, a recess, an elevation, a sphere, a hemisphere, a conical shape and/or a pyramidal shape. Several ones of these different possible markings of the same or of different kinds are also possible. With such markings, the position of a model support of an abutment model can be very precisely identified relative to the marking.

The flat surface of the insert can comprise a geometric pattern. The pattern can comprise, for example, lines, circular, angular and/or polygonal surfaces or any other shape, these lines, surfaces and/or other shapes setting themselves apart from the other areas of the flat surface, for example in terms of color. A difference in terms of color can here result from different shades of gray including black and/or multicolored. The geometric pattern can also result, for example, from recesses and/or elevations, wherein the recesses and/or elevations can comprise various shapes, colors and/or dimensions. By the geometric pattern on the flat surface of the insert and/or the model support of the abutment model, for example a relative position of the insert can be precisely determined.

The geometric pattern can be embodied symmetrically, rotationally symmetrically and/or asymmetrically. For example, for the same model supports, the same geometric patterns can be used on the flat surface, however, different patterns can also be used for the same model supports.

The flat surface of the insert can be circular, square, rectangular, triangular, hexagonal, polygonal or elliptic or have any other shape.

The flat surface of the insert can be oriented horizontally in a working position. By the horizontal orientation of the flat surface, for example in a scanning operation of the mounted model support of the abutment model, certain areas can be prevented from being covered.

The insert can comprise an introduction inclination in the second area. The introduction inclination can be used to facilitate the fitting of an insert into another component which can receive the insert.

A pot for receiving an insert according to the invention can comprise at least one magnet and at least one recess and/or at least one elevation in, under and/or on a bottom surface of the pot. The at least one magnet of the pot can be used to pull the insert, which comprises at least one magnet in the second area, into the pot. The at least one recess and/or elevation in, under and/or on the bottom surface of the pot can be used to determine the relative position of the pot and the insert within certain limits. By the shape and/or dimension of the at least one recess and/or the at least one elevation, the relative position of the pot and the insert can be determined, for example, to less than 5, 4, 3, 2 or 1 mm. Moreover, the relative position for the positioning can be variable within a range of more than 1, 2, 3, 4 or 5 mm. The at least one recess and/or the at least one elevation can comprise a groove, a flute, a rib, a hole, a pin and/or a peg.

The pot can comprise a recess, an elevation and/or a marking at an upper edge. Thereby, it is possible to determine a relative position of the pot, wherein the position can be used as reference, for example in a scanning device.

The pot can comprise at least one rib at an outer surface. The at least one rib can, for example, define the positioning of the pot and/or be used for holding the pot. For example, the pot can also comprise an introduction inclination in the lower area (i.e. in the area of the bottom surface).

The pot can receive an insert according to the invention. Thereby, easy handling of the insert and/or the assembled pot and insert can be ensured.

The at least one magnet of the pot and the at least one magnet of the insert can pull the insert in the direction into the pot. This permits, for example, to facilitate the introduction of the insert into the pot.

The at least one magnet of the pot and/or the at least one magnet of the insert can, for example, also consist of a material which is attracted by a magnet. If, for example, two areas for magnets each are provided in the insert and in the pot, the insert can for example comprise two magnets and the pot can comprise two areas with a material which is attracted by the magnets. However, for example the insert and the pot can each comprise a magnet and an area with a material which is attracted by the magnet. In this connection, reference is made to the pairs of magnetic poles which are complementary oriented as described above.

The at least one gripping device of the insert can project beyond the upper edge of the pot, and the at least one gripping device can preferably not be in contact with the upper edge of the pot.

The flat surface of the insert can be located within the pot when the pot and the insert are assembled, i.e. the flat surface of the insert does not project beyond the upper edge of the pot. The optically detectable marking of the insert can project beyond the upper edge of the pot, however, it can also be located within the pot or be flush with the upper edge of the pot. If the flat surface comprises different optically detectable markings, these can be located within the pot, project beyond the upper edge of the pot and/or be flush with the upper edge of the pot. For example, the flat surface of the insert can also be flush with the upper edge of the pot or project beyond the upper edge of the pot.

A scanning device can comprise scanning means as well as at least one pot according to the invention.

Furthermore, the scanning device can comprise at least one insert according to the invention. This permits, for example, to hold a model support of an abutment model and scan it by means of the device.

Furthermore, the scanning device can comprise at least one device for holding a model support of an abutment model according to the invention. This also permits, for example, to hold a model support of an abutment model and scan it by means of the device.

In a scanning method, at least one abutment model can be scanned by means of the scanning device according to the invention, wherein the at least one abutment model can be mounted on the at least one insert according to the invention or held by a device for holding a model support of an abutment model according to the invention. By the use of the insert, a precise determination for example of the position of the abutment model relative to the attachment geometry of an implant and/or the height of the abutment model relative to the attachment geometry can be accomplished.

For a plurality of attachment geometries onto which one model support of an abutment model each can be mounted, for example one holder or one insert, respectively, can be provided each. Thus, the holder matching a determined model support can be selected without it being necessary to exchange an attachment geometry in the holder or in the insert, respectively, as for example one holder or one insert, respectively, is assigned to each of the plurality of attachment geometries. Without this assignment, an exchange of an attachment geometry of an insert would be, for example, necessary if a different attachment geometry is to be used.

The position of the at least one abutment model can be determined relative to the attachment geometry of the at least one insert onto which the at least one abutment model is mounted.

A height of the at least one abutment model can be determined relative to the attachment geometry by also scanning the step of the insert in the process. The attachment geometry can project beyond the step, the relative position being defined. If now the step is also scanned during the scanning process, the height of the abutment model relative to the attachment geometry can be determined from this.

A relative spatial position of the at least one abutment model can be determined with respect to the attachment geometry of the at least one implant by also scanning the optically detectable marking of the insert. The defined relative position of the marking and the attachment geometry and the thus resulting relative spatial position of the abutment model with respect to the attachment geometry can be used for further processing.

During scanning, measured data can be obtained, preferably shape data which can indicate the geometry of an abutment. By means of these data, a corresponding tooth replacement part can then be produced.

The measured data can be stored and/or forwarded. The measured data can also be evaluated, for example to acquire on the one hand the geometry of the abutment and on the other hand the relative position of the abutment model and the attachment geometry. Moreover, the production of the tooth replacement part and/or scanning can be performed at other locations than those where the measured data are evaluated. However, the steps can also be carried out at the same location.

In the scanning method which scans, for example, an abutment model by means of the scanning device according to the invention, the insert which comprises the abutment model can be located at any position within an area the device scans. It is thus for example possible to use a plate or a receiving means of another shape on which the insert or inserts can be applied. Moreover, one or several pots according to the invention which each comprise one or several inserts according to the invention can be applied onto the plate or onto the receiving means. For the scanning operation, however, for example certain areas of the plate or of the receiving means can be determined which are then to be scanned.

In one method of producing an abutment, an abutment model can be scanned according to the scanning method of the invention, wherein an outer shape of the abutment can result from the measured data of the scanned abutment model. The abutment can then be modeled by means of the measured data. Moreover, an attachment geometry of the abutment can be modeled, so that the abutment can be mounted onto the attachment geometry of a corresponding implant.

In a method of producing a tooth replacement part comprising an abutment, an abutment model can be scanned according to the scanning method of the invention, wherein an inner shape of the tooth replacement part can result from the measured data of the scanned abutment model. For example, a crown or a bridge or something else can be mounted onto the abutment.

The tooth replacement part can, for example, be made from plastics, glass-fiber reinforced plastics, glass-fiber reinforced copolyamide, cobalt or a cobalt alloy, a chromium-cobalt alloy, titanium or a titanium alloy, gold or a gold alloy, ceramics, zirconium ceramics or alumina, but it is not restricted thereto.

BRIEF DESCRIPTION OF THE DRAWINGS

Advantageous embodiments of the invention are illustrated with reference to the enclosed figures. In the figures.

DETAILED DESCRIPTION

Figure 1A:
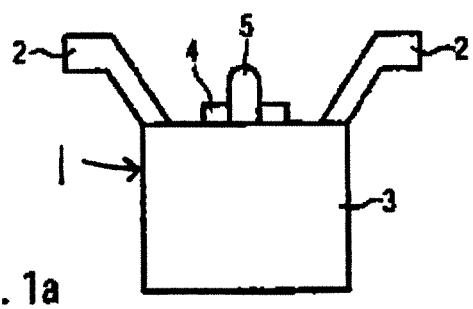
FIGS. 1a-1d show a schematic representation of an insert for holding a model support.

In FIG. 1a, a schematic representation of an insert 1 for holding a model support of an abutment model is shown in a side view. The insert 1 represents a special embodiment of a general holder for holding a model support of an abutment model. The shown insert comprises two gripping means 2 which start from a flat, circular surface 6 and here face obliquely upwards and project beyond the limit of this flat surface 6. Moreover, the insert 1 comprises a step 4 which is here embodied in a disk shape with a circular cross-section and is located on the flat surface 6. For the flat surface 6 as well as independently for the step 4, other cross-sectional shapes than circular are possible, such as square, rectangular, triangular, hexagonal, polygonal or elliptic, or any other shape. Moreover, an optically detectable marking 5 is located on the flat surface 6 which is here embodied as pin with a hemispherical end. However, the pin can also have an acute or an obtuse end or an end having another shape. The optically detectable marking 5 can also comprise a peg, a hologram, a bar code, a pattern code, a groove, a flute, a recess, an elevation, a sphere, a hemisphere, a conical shape and/or a pyramidal shape. The marking can also comprise a combination of two or several ones of these shapes.

Figure 1B:
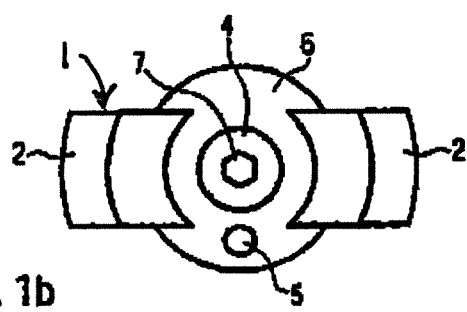

FIG. 1b shows a representation of the insert 1 of FIG. 1a from above. In the center of the step 4 which here has a circular design, there is the attachment geometry 7 of an implant which here has a hexagonal shape. The attachment geometry 7, however, can also be round, triangular, octangular, rectangular or have any other shape.

Figure 1C:
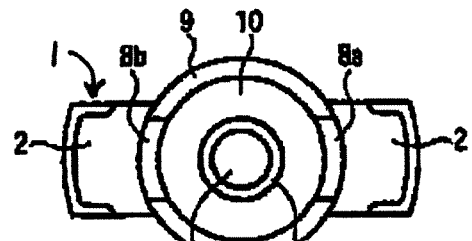

FIG. 1c shows a representation of the insert 1 of FIG. 1a from below. An inner hollow cylinder 11 is surrounded by an outer cylindrical wall 9, the outer wall 9 comprising two recesses 8a, 8b. The inner hollow cylinder 11 comprises an area 12 into which, for example, a circular magnet can be introduced. The inner hollow cylinder and the corresponding magnet, however, can also have a cross-section other than circular, for example triangular, square, rectangular, elliptic or any other cross-section.

Figure 1D:
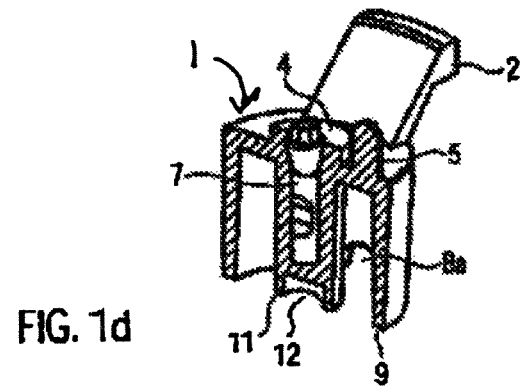

FIG. 1d shows a three-dimensional schematic sectional representation of the insert 1 of FIG. 1a. In the hollow cylinder 11, there is an insertion part with an attachment geometry of an implant 7. Different insertion parts with different shapes and different attachment geometries can be used, wherein one insertion part each is preferably firmly connected with an insert. A so-called Wax Up Sleeve (model support) can be applied onto the insertion part of the insert (also see FIG. 5) around which an abutment model can be modeled.

Figure 2A:
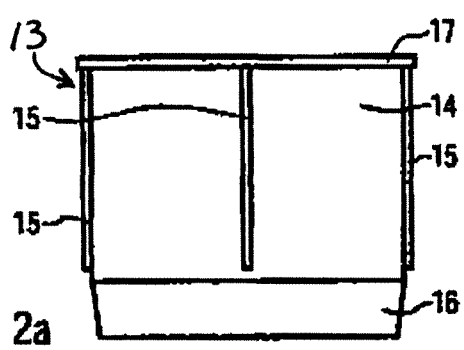
FIGS. 2a-d show a schematic representation of a pot for receiving an insert for holding a model support.

FIG. 2a shows a schematic representation of a pot 13 for receiving an insert 1 for holding a model support of an abutment model in a side view. This pot 13 represents an example of a general receiving means of a holder. On its outer surface, the pot 13 comprises several ribs 15 which can for example define the positioning of the pot 13 and/or can be used for holding the pot 13. The represented pot 13 moreover comprises an introduction inclination 16 in the lower area. However, the pot 13 might also only comprise one rib 15.

Figure 2B:
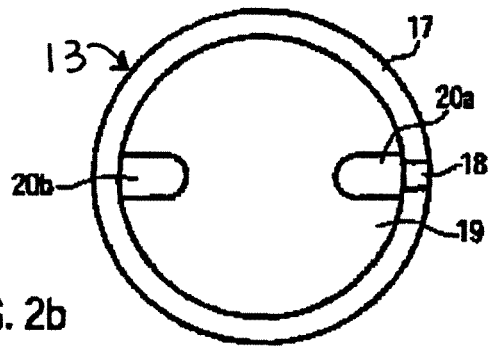

FIG. 2b shows a representation of the pot 13 of FIG. 2a from above. The pot 13 comprises a recess 18 at its upper edge 17 which permits, for example, to determine a relative position of the pot 13. On its bottom surface 19, the represented pot 13 comprises two elevations 20a, 20b, which fit, for example, into the two recesses 8a, 8b of the insert 1 shown in FIG. 1. The elevations 20a, 20b and the recesses 8a, 8b can thus serve a relative positioning of the insert 1 and the pot 13 which is at least partly defined. Instead of the recess 18, the pot 13 can comprise, for example, an elevation and/or a marking, or else a combination of a recess, elevation and/or marking. These can have various sizes, permitting a defined though variable positioning.

Figure 2C:
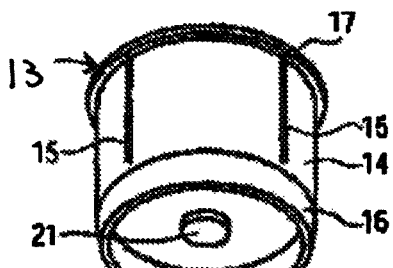

FIG. 2c shows a three-dimensional representation of the pot 13 with a viewing direction from the bottom, wherein the area 21 provided for a magnet in the bottom surface 19 of the pot 13 can be seen. The area 21 does not have to be round, it can also be triangular, square, rectangular, elliptic or have any other shape. The ribs 15 at the outer surface 14 of the pot 13 in this representation end above the introduction inclination 16. The ribs 15, however, can also reach into the area of the introduction inclination 16, or else be present along the total height of the pot 13; the same applies if, for example, only one rib 15 is present.

Figure 2D:
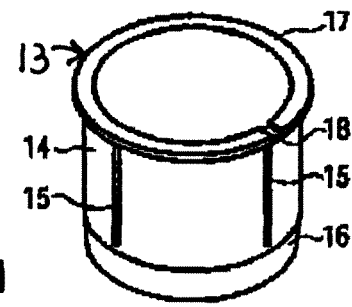

FIG. 2d shows a three-dimensional representation of the pot 13 with a viewing direction from above.

Figure 3:
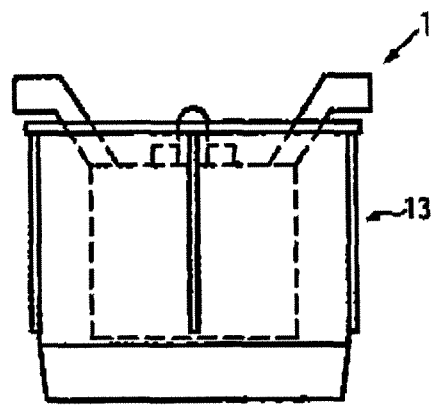
FIG. 3 shows a schematic representation of a pot with an inserted insert.

FIG. 3 shows a pot 13 that contains an insert 1. It can be seen that the gripping means 2 of the insert 1 are not in contact with the upper edge of the pot 13. The position of the insert 1 results from the dimensioning of the bottom surface 19 of the pot as well as from the dimensioning of the lower edge of the insert 1. If the insert 1 and the pot 13 have a circular cross-section, as it is shown, the insert 1 can be pulled downwards within the pot 13 by the magnets of the insert 1 and the pot 13 if the corresponding magnets are correspondingly oriented. However, as exact centering is not essential, the diameter of the insert 1 and the pot 13 can clearly deviate from each other. Thereby, the insert 1 can be easily loosely inserted into the pot 13.

For the geometry of the holder 1 and the receiving means 13 and the pot 13, respectively, which is shown in FIG. 3, variable positioning is possible. That means, the holder 1 can be shifted in a direction horizontal in FIG. 3 or positioned in another position in the horizontal direction. Here, the height of the holder 1 (distance to the receiving means 13), however, remains unchanged.

Figure 4:
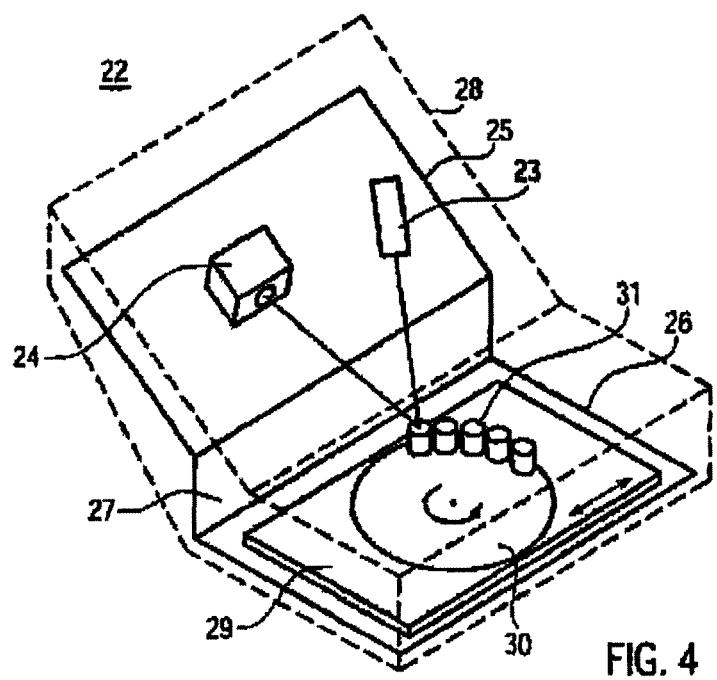
FIG. 4 shows a schematic representation of a device for scanning tooth models.

In FIG. 4, a device 22 for scanning tooth models is shown in a three-dimensional schematic representation. The device has a first base plate 26, at which an inclined second base plate 25 is arranged via a support 27. The second base plate 25 is arranged at an angle of 20 degrees to 80 degrees, or 35 degrees to 60 degrees, preferably about 45 degrees with respect to the first base plate 26. The second base plate 25 carries an optical scanner system 23, 24 which can scan models within a scanning range. The scanning range is also at an angle of 20 degrees to 80 degrees, preferably 35 degrees to 60 degrees, more preferred about 45 degrees or more or less than 45 degrees with respect to the first base plate 26 or base plate 30.

The abutment model or models 31 can be arranged on a base plate 30, wherein the abutment models 31 can be applied on an insert 1 according to the invention which is located in a pot 13 according to the invention. The pot 13 itself can in turn be introduced in holders on the base plate 30 and fixed there. The base plate 30 is designed as rotary table and has an axis of revolution, wherein the rotary table can be rotated into one direction or else into both directions about the axis. The axis can moreover be shifted in the horizontal direction by correspondingly moving a plate 29.

The pot 13 can be firmly connected to the scanning device. Each of the inserts 1 can be easily exchanged, as described above.

The device for scanning tooth models shown in FIG. 4 can moreover have a lid 28 which can cover the optical components 23, 24. The lid is used to reduce or exclude ambient light and to protect the optical components 23, 24 from dust or the like.

Figure 5A:
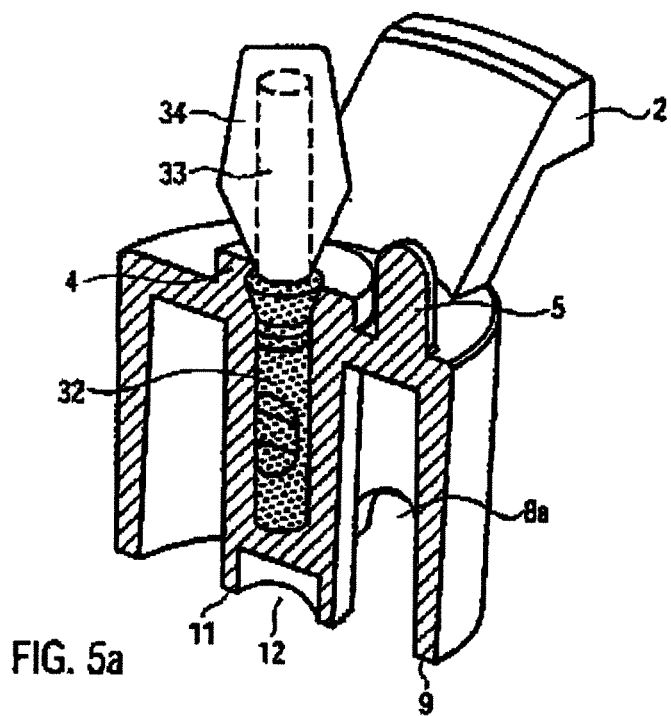
FIGS. 5a-b show a schematic representation of an insert with an applied Wax Up Sleeve and a modeled abutment model.
Figure 5B:
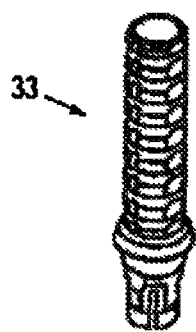

FIG. 5a shows a representation of an insert 1 which comprises an insertion part 32 on which a Wax Up Sleeve 33 (here shown in a stylized manner) is applied. A representation of an exemplary Wax Up Sleeve 33 is shown in FIG. 5*b*. An abutment model 34 is applied on the Wax Up Sleeve 33.

The Wax Up Sleeve is here used as a model support of an abutment model. For preparing the model, however, the Wax Up Sleeve can also be e.g. shortened. It can then also form a part of the abutment model, however it then remains the model support of the same.

In a scanning method that uses a scanning device 22 according to the invention, for example an insert 1 as it is shown in FIG. 5*a* can be scanned. The outer shape of the abutment model can be scanned. Moreover, the position and/or the height of the abutment model relative to the attachment geometry 7 of the insertion part 32 can be determined by also scanning the step 4 and/or the optically detectable markings 5 of the insert 1. By scanning, measured data can be obtained, preferably shape data which represent the geometry of the abutment model. The measured data can be stored, processed and/or forwarded. The measured data can then be used, for example, to determine the outer shape of an abutment and/or the inner shape of a tooth replacement part. The abutment and/or the tooth replacement part can then be modeled and/or produced.

The invention claimed is:

1. Device for holding a model support of an abutment model, comprising a holder and a receiving means, wherein the holder comprises at least one of a magnet and a magnetic material, and wherein the holder can be mounted onto the receiving means, and wherein the holder can be positioned variably with respect to the receiving means,
   wherein the holder comprises a first and a second area, and
   in the first area comprises a flat surface, wherein a step is located on or in the flat surface in the center of which there is an area which comprises an attachment geometry of an implant and onto which the model support of the abutment model can be mounted, and
   in the second area comprises a means that permit the positioning of the holder.

2. Device according to claim 1, wherein the holder comprises the at least one magnet and the receiving means comprises at least one of a magnet and a material that is attracted by the at least one magnet of the holder.

3. Device according to claim 1, wherein the holder comprises the at least one magnetic material and the receiving means comprises a magnet.

4. Device according to claim 1, wherein the holder and the receiving means are each shaped such that variable positioning is only possible within a restricted area.

5. Device according to claim 4, wherein the area to which the variable positioning is restricted has different dimensions in different directions in space.

6. Device according to claim 1, wherein the distance between the holder and the receiving means is determined by the shape of the holder and of the receiving means.

7. Device according to claim 1, wherein at least one of the holder and the receiving means comprises at least one of a groove, flute, hole, pin, peg, recess and elevation.

8. Device according to claim 7, wherein the holder and the receiving means each have at least one groove, flute, hole, pin, peg, recess elevation and that are shaped in a reversed manner.

9. Device according to claim 1, wherein the holder comprises an optically detectable marking.

10. Device according to claim 1, wherein the holder comprises at least one gripping means in the first area.

11. Device according to claim 10, wherein the at least one gripping means starts from the flat surface.

\* \* \* \* \*

UNITED STATES PATENT AND TRADEMARK OFFICE
CERTIFICATE OF CORRECTION

| | | |
|---|---|---|
| PATENT NO. | : 8,448,928 B2 | Page 1 of 1 |
| APPLICATION NO. | : 12/682085 | |
| DATED | : May 28, 2013 | |
| INVENTOR(S) | : Weber | |

It is certified that error appears in the above-identified patent and that said Letters Patent is hereby corrected as shown below:

In the Claims:

In column 10, line 26 claim 8 after "recess" insert -- and --.

Signed and Sealed this
Sixth Day of August, 2013

Teresa Stanek Rea
*Acting Director of the United States Patent and Trademark Office*